United States Patent [19]

Millstein

[11] Patent Number: 4,708,649
[45] Date of Patent: Nov. 24, 1987

[54] OCCLUSAL CLEARANCE INDICATOR

[76] Inventor: Philip L. Millstein, 15 Langdon St., Cambridge, Mass. 02138

[21] Appl. No.: 793,137

[22] Filed: Oct. 31, 1985

[51] Int. Cl.$^4$ ............................................. A61C 9/00
[52] U.S. Cl. ....................................................... 433/71
[58] Field of Search .................................... 433/70, 71

[56] References Cited

U.S. PATENT DOCUMENTS 3,959,881  6/1976  Kokal, Jr. ............................. 433/70
4,482,321  11/1984  Tabor et al. ........................ 433/71
4,547,155  10/1985  Adler .................................. 433/70

Primary Examiner—Robert Peshock
Attorney, Agent, or Firm—Wolf, Greenfield & Sacks

[57] ABSTRACT

An occlusal clearance indicator for measuring the distance between a tooth prepared to receive a cast restoration and an opposing tooth.

3 Claims, 4 Drawing Figures

OCCLUSAL CLEARANCE INDICATOR

BACKGROUND OF THE INVENTION

This invention relates in general to dentistry, and more particularly to a device and a method for measuring the occlusal clearance when preparing a tooth for a cast restoration.

The occlusal clearance is the space created between two opposing teeth in preparing one or both of them for a cast restoration. Cast restorations are commonly known as caps, crowns and bridges. They involve replacing a portion of a tooth with an artificial replica which is secured to a remaining portion of the tooth or is secured to the adjacent teeth. To attach a cast restoration to a remaining portion of a tooth, there must be a minimum space between the remaining portion of the tooth and the opposing teeth when the two rows of teeth are at normal occlusion, that is, when the two rows of teeth are brought together in a closed position. Ordinarily, a dentist grinds down the remaining portion of the tooth to create this minimum space. An inadequate space can lead to a subsequent failure of the cast restoration. The minimum space (occlusal clearance) required for cast restorations is approximately 1 millimeter for metal restorations and 2 millimeters for porcelain to metal restorations.

An occlusal clearance indicator is a device used to measure the occlusal clearance. Present methods and devices for measuring the occlusal clearance are unreliable. In one method, the dentist, with the aid of a mouth mirror, has the patient bring the opposing rows of teeth together to normal occlusion and the dentist then attempts to make a subjective assessment of the clearance between the tooth receiving the restoration (tooth preparation) and the opposing tooth or teeth. The occlusal clearance, however, is obscured by the tongue, saliva, muscles of the cheeks and diminished light. It is difficult, if not impossible, to make accurate and visual assessments of the occlusal clearance intraorally.

Wax or other impression material is also used to measure occlusal clearance. The dentist places the wax over the tooth preparation and has the patient bite into it. The dentist then inspects the wax intraorally or removes it and emits light through it to estimate the wax thickness. This method does not result in reliable measurements. It is only an estimate of the occlusal clearance, not a direct measurement. Furthermore, the wax may stick to the teeth and distorts the impression when removing the wax, making the procedure even unsuitable for an estimate. Using impression materials can also be time-consuming. Many dentists use a material which must cool or set before it can be observed. Where multiple measurements are required, it is a particularly time consuming method for measuring occlusal clearance.

Recently, blotting paper has been used to measure occlusal clearance. This technique suffers many drawbacks. First, a three dimensional representation (a dental indentation) cannot be recorded on blotting paper. A dental indentation will enable the dentist to visually determine how much tooth structure is to be removed prior to completing sufficient occlusal reduction. Blotting paper is also awkward to handle. Customarily, two or more layers of blotting paper have to be cut into strips and held together by forceps. Sometimes marking paper is also wrapped around the blotting paper and must also be held by the forceps. These manipulations are time-consuming and undesirable.

It has been suggested to use rubber bands to measure occlusal clearance. If the rubber band pulls from between the teeth, then the space is wider than the rubber band. If the rubber band is held by the teeth, then there is insufficient space between the teeth. As with blotting paper, this method does not use standard dental material and a dental indentation cannot be recorded on it.

Finally, a calibrated ball gauge has been used to determine whether there is sufficient occlusal clearance for cast restoration. The gauge is essentially a probe having a ball on its end. The ball is slipped between the tooth preparation and the opposing tooth or teeth at normal occlusion to verify if there is sufficient occlusal clearance for a cast restoration. The ball may have a diameter calibrated to verify the desired clearance. As with the above methods, the ball gauge does not record an observable dental indentation. It is also not disposable and relatively expensive to manufacture.

The present invention overcomes the above limitations and has additional advantageous features.

SUMMARY OF THE INVENTION

It is an object of the invention to provide an occlusal clearance indicator that indicates how much tooth structure must be removed to achieve the minimum clearance.

Another object of the invention is to provide an occlusal indicator that can be manufactured in many thicknesses to suit the needs of the particular patient and the particular dentist.

Another object of the invention is to provide an occlusal clearance indicator that is inexpensive to manufacture.

Another object of the invention is to provide an occlusal clearance indicator that is easy to use.

Still another object of the invention is to provide an occlusal clearance indicator that may be used quickly and hygienically.

According to the invention, a strip of impressionable material is provided. The strip is preferably made from styrofoam, is 10 millimeters in width and is between 1.0 and 5.0 millimeters in thickness.

Also according to the invention, a method for measuring occlusal clearance is provided. A strip of impressionable material is placed between a tooth preparation and the opposing tooth. The patient then brings the teeth to normal occlusion. The patient then opens and the strip is removed. The strip is then inspected for indentations.

These and other features of the invention are set forth below with more particularity.

DETAILED DESCRIPTION OF THE DRAWINGS

Figure 1:
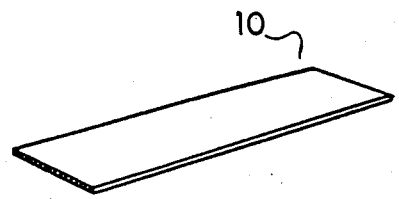
FIG. 1 is a perspective view of an embodiment of the invention.
Figure 2:
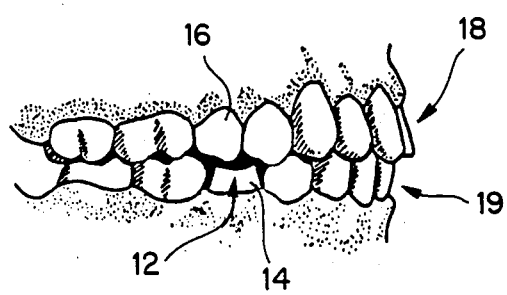
FIG. 2 shows teeth including one prepared for a cast restoration at normal occlusion.

FIG. 1 illustrates an embodiment of the invention. The indicator 10 is made from an impressionable material, preferably a soft moldable polystyrene material and most preferably styrofoam. The occlusal clearance 12 between a tooth preparation 14 ground for restoration and the opposing tooth 16 is shown in FIG. 2. The teeth are shown at normal occlusion. The occlusal clearance is measured when the teeth are at normal occlusion.

Figure 3:
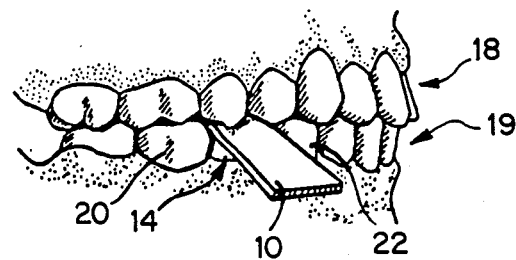
FIG. 3 illustrates the method for measuring occlusal clearance with the occlusal indicator of the invention.

To measure the occlusal clearance, the indicator 10 is placed over the tooth preparation 14 when the patient's mouth is opened. Next the upper and lower rows of teeth 18 and 19 are brought into normal occlusion as shown in FIG. 3. The proper width of the indicator 10 is such that it fits between teeth 20 and 22 on either side of and immediately adjacent ground tooth 14 so that it will not interfere with normal occlusion. The desirable width may therefore differ for each particular tooth preparation. Generally, the desirable width of the indicator will be between about 4 and 15 millimeters.

Figure 4:
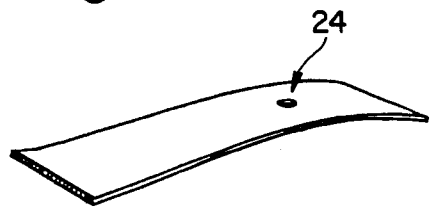
FIG. 4 shows the occlusal indicator of FIG. 3 after it is removed from between the teeth.

The patient then opens the jaws separating the two rows of opposing teeth and the indicator is removed for inspection. An indentation 24 in the indicator 10, as suggested in FIG. 4, means that the distance between the opposing teeth at the spot indicated by the indentation is less than the thickness of the indicator. A space of approximately 1 millimeter is required for a metal crown, and 2 millimeters are required for a porcelain crown. An indentation in a 1 millimeter thick indicator shows that there is not enough space for a metal crown. Similarly an indentation in a 2 millimeter thick indicator shows that there is not enough space for a porcelain-coated crown. If two opposing teeth were being restored then the indicator would be two times the thickness required for a single restoration or approximately two millimeters for opposing metal crows and four millimeters for opposing porcelain crowns.

The indentation is a three-dimensional representation of the portion of the teeth that must be removed to provide the required clearance. The dentist can then continue grinding and testing with indicators until a sufficient space is provided. A sufficient space is provided when a test results in no indentation in the indicator 10.

Styrofoam is ideal because an occlusal-dental print, the indentation 24, can be easily made in it. Styrofoam is also flexible and will bend according to the contours of the teeth lessening the probability of false indentations. Furthermore, because of styrofoam's somewhat frictionless properties, it may also be used to record excursive movements as they relate to adequate occlusal clearance. Excursive movements are those commonly known as grinding movements of the teeth. The changed position of opposing teeth due to these movements can require further grinding of a tooth preparation to ensure adequate space for a cast restoration.

The styrofoam indicators can be calibrated to many different thicknesses to suit the needs of the particular patient, the type of material used for the cast restoration, and the dentist's preference for a particular distance between the tooth preparation and the opposing tooth or teeth. The styrofoam may be packaged in different thicknesses in sterile disposable units.

The indicator may also be manufactured in various shapes to facilitate its placement.

Laboratory technicians often fabricate crowns and complex restorations on dental casts where there have been insufficient or excessive tooth reduction. Calibrated indicators could also be used by these tehnicians prior to the fabrication of a restoration to determine just how much space is available. With this information a technician could communicate with the dentist and both could make educated choices as to the proper design of a prosthesis and the most suitable material selection.

It should be understood that various changes and modifications of the embodiment shown in the drawings may be made within the scope of this invention. Thus it is intended that all matter contained in the above description or shown in the accompanying drawings shall be interpreted in an illustrative and not limiting sense.

What I claim is:

1. An occlusal indicator for measuring the occlusal clearance between a tooth ground down for a cast restoration and an opposing tooth, said ground down tooth lying between adjacent teeth, the indicator comprising,
    a strip of polystyrene-type impressionable material, said strip of material being between about 1 and 2 millimeters in thickness, said 1 millimeter the amount of space required for placing a metal restoration and said 2 millimeters being the amount of space required for placing a pocelain-coated restoration, and said strip being between about 4 and 15 millimeters in width, the width being no wider than the distance between the adjacent teeth such that the width of the strip will lie completely between the adjacent teeth at normal occlusion.

2. In preparing a tooth for a cast restoration, a method for measuring the occlusal clearance between a tooth ground down for a cast restoration and an opposing tooth, said ground down tooth lying between adjacent teeth, comprising,
    placing a strip of impressionable material between 1 and 2 millimeters in thickness and 4 and 15 millimeters in width between said ground down tooth and said opposing tooth such that the width of the strip will lie completely between the adjacent teeth at normal occlusion,
    bringing the teeth to normal occlusion,
    removing the strip of impressionable material, and
    inspecting the strip of impressionable material for indentations, the absence of any indentation indicating sufficient clearance for the cast restoration.

3. A method as claimed in claim 2 wherein said impressionable material is a polystyrene-type material.

* * * * *